United States Patent [19]

Uemura et al.

[11] Patent Number: 4,692,331
[45] Date of Patent: Sep. 8, 1987

[54] GAMMA-GLOBULIN PREPARATION FOR INTRAVENOUS ADMINISTRATION

[75] Inventors: Yahiro Uemura, Hirakata, Japan; Satoshi Funakoshi, Los Angeles, Calif.

[73] Assignee: The Green Cross Corporation, Osaka, Japan

[21] Appl. No.: 583,268

[22] Filed: Feb. 24, 1984

[30] Foreign Application Priority Data

Feb. 25, 1983 [JP] Japan .................................. 58-31460

[51] Int. Cl.$^4$ .......................................... A61K 39/395
[52] U.S. Cl. ...................................... 424/85; 530/387
[58] Field of Search .................. 260/112 B, 112 R; 424/85, 101; 530/387

[56] References Cited

U.S. PATENT DOCUMENTS

| | | | |
|---|---|---|---|
| 4,124,576 | 7/1978 | Coval | 424/101 |
| 4,165,370 | 8/1979 | Coval | 424/85 |
| 4,362,661 | 12/1982 | Ono et al. | 424/101 |
| 4,374,763 | 2/1983 | Takage | 424/177 |
| 4,482,483 | 11/1984 | Curry et al. | 424/85 |

OTHER PUBLICATIONS

Rahn, Physical Method of Sterilization of Microorganisms, Bact. Rev., 9, pp. 1 and 24, 1945.
Deiwest Abstract of Japanese Laid Open Patent Application No. 3047–515, 1978.

*Primary Examiner*—Blondel Hazel
*Attorney, Agent, or Firm*—Cushman, Darby & Cushman

[57] ABSTRACT

A dry γ-globulin preparation capable of intravenous injection which is obtainable by polyethylene glycol fractionation of plasma is improved in its water-solubility and stability against increase of anticomplement activity and decrease of antibody titer by purifying the γ-globulin fraction with respect to protein to render the residual polyethylene glycol substantially not detectable in its 5% W/V solution, adding 0.2 to 2 parts by weight of glucose based on 1 part of γ-globulin, and lyophilizing its solution.

4 Claims, No Drawings

GAMMA-GLOBULIN PREPARATION FOR INTRAVENOUS ADMINISTRATION

BACKGROUND OF THE INVENTION

This invention relates to an improvement in preserving stability of an intravenously administrable human gamma-globulin dry preparation obtainable by polyethylene glycol fractionation of the human plasma.

Polyethylene glycol (hereinafter referred to as PEG) is a substance widely used as a stabilizer or a precipitant for protein and, because of its extremely low toxicity, is used also in the preparation of biological pharmaceuticals. For example, Polson et al has purified γ-globulin by adding to human plasma PEG to a certain concentration and separating the precipitated protein (U.S. Pat. No. 3,415,804). The intravenously administrable γ-globulin preparation is prepared by lyophilizing the product obtained by PEG fractionation mentioned above. But, when the lyophilized preparation is dissolved in distilled water for injection use at the time of administration, it often does not go into solution rapidly.

Some of the present inventors made an extensive study on this point and found that the dissolving velocity was affected by PEG and that when the content of contaminating PEG was below a specified level the dry preparation had an improved water-solubility to dissolve rapidly in water, and proposed a method of producing a plasma protein preparation based on this novel information (Japanese Patent Application No. 8911/83). The feature of the prior invention comprises, in a plasma protein dry preparation comprising human plasma protein prepared by PEG fractionation method, removing PEG prior to drying treatment so as to give a PEG concentration of 0.05% W/V or less when the preparation is dissolved in water to give a protein concentration of about 20% W/V.

When the content of PEG in γ-glogulin preparation obtainable by fractionation by use of PEG is decreased, the stability of the γ-globulin against deterioration with time becomes poor accompanied by the decrease in antibody titer and increase in anticomplement activity. It was found out that this tendency can be prevented markedly by addition of a sufficient amount of glucose for stabilizing the γ-globulin to an aqueous solution of γ-globulin followed by lyophilization.

DETAILED DESCRIPTION OF THE INVENTION

Thus, according to this invention, there is provided an intravenously administrable γ-globulin dry preparation obtainable by fractionating human plasma by polyethylene glycol, which is substantially free of remaining polyethylene glycol, which comprises γ-globulin and glucose added in an amount sufficient for stabilizing the γ-globulin.

The γ-globulin in this invention is obtained by a PEG fractionation method and the preparation thereof generally contains residual PEG. As the method for preparing an intravenously administrable γ-globulin by the use of PEG, there may be mentioned, for example, one which comprises adding PEG to concentrations of 4% W/V, 5% W/V and 12% W/V successively. Japanese Patent Application Kokai (Laid-Open) No. 20415/78. But the present invention is not limited to this method of preparation and can be applied widely for improving intravenously administrable γ-globulin preparations utilizing PEG.

The PEGs referred to in this invention are those which can be utilized for plasma fractionation and generally have an average molecular weight of 3000 to 20,000. The γ-globulin dry preparation substantially free of PEG herein referred to means that PEG can not be detected in an aqueous solution of γ-globulin in an amount of about 5% W/V in terms of protein according to a colorimetry having a superior detection sensibility. The colorimetric method utilizes the formation of barium-iodine complex resulting from the combination of PEG with barium and iodine, which has an absorption in the 535 nm band *Microchemical Journal* 20, 190–192 (1975).

The removal of contaminating PEG in the γ-globulin fraction capable of intravenous administration may be carried out according to known methods of protein purification by, for example, fractionation by use of alcohol, salting out, or treatment with a synthetic adsorbent as those of the nonpolar styrene-divinylbenzene type. The alcohol fractionation method is carried out by adding to an aqueous solution containing 1 to 10% W/V of the γ-globulin fraction contaminated with PEG a neutral salt such as sodium chloride and magnesium chloride to a concentration of 0.04 to 0.75 mol, adding 15 to 40% V/V of ethanol thereto, then treating the mixture at pH 5 to 8 at a temperature of 0° to $-10°$ C. for 30 minutes to 24 hours, and recovering the precipitate formed. The product is, if desired, subsequently subjected to dialysis to regulate the salt concentration. The salting-out method is carried out by preparing an aqueous solution containing 1 to 10% W/V of plasma protein contaminated with PEG, adding ammonium sulfate thereto to 25 to 70% saturation, treating the resulting mixture at pH 5 to 7 at a temperature of 20 to 0° C. for 30 minutes to 24 hours, and recovering the precipitate formed. The product is, if desired, subsequently subjected to dialysis to regulate the salt concentration.

The symbol "% W/V" or "% V/V" means herein a percentage of a solute by weight or by volume per a solution by volume, respectively.

The treatment with a synthetic adsorbent is carried out by use of a nonpolar styrene-divinylbenzene copolymer, which has a fine-grained surface and is hydrophobic. Commercially available adsorbents include HIGH POROUS POLYMER (made by Mitsubishi Kasei, Inc.), WAZI (made by Mitsubishi Kasei, Inc.), and AMBERLITE XAD (made by Rohm and Hass, Inc.). The synthetic absorbent is used preferably after being washed with 10 to 70% W/V of ethanol, of 0.05 to 1.0 N hydrochloric acid or sodium hydroxide. The adsorption treatment is carried out, batchwise or by a column method, by contacting an aqueous solution of γ-globulin contaminated with PEG as it is with the adsorbent to remove the PEG from the aqueous solution fraction by adsorption on the synthetic adsorbent.

Since the method of alcohol fractionation and that of salting out involve the necessity of removing again the inorganic salt or alcohol used in fractionation by lyophilization or dialysis after the treatment, the treatment with a synthetic adsorbent is preferred.

The γ-globulin solution from which the PEG has been thus removed is sterilely filtered in a conventional manner, then glucose is added to the solution as a stabilizer in an amount sufficient for stabilizing the γ-globulin. The amount to be added is about 0.2 to 2 parts by weight based on 1 part by weight of γ-globulin which is dissolved in a solution of 5 to 20% W/V. The solution is lyophilized to give a dry preparation. The preparation is dispensed so that each unit contains 500 to 10,000 mg of γ-globulin according to the package unit. It is stored avoiding a high temperature condition and, when using, dissolved in distilled water for injection use and administered intravenously.

The dosage is generally 500 to 3000 mg in terms of γ-globulin per one time for adults and 250 to 1500 mg for infants.

As a safety test, an acute toxicity test was carried out. A 10% solution of the preparation was administered in a total amount of 0.5 ml/an animal and 1.0 ml/an aminal to two groups each consisting of 5 mice via the tail vein of the mouse. No abnormality was recognized in 7 days' observation.

Since the γ-globulin preparation for intravenous administration of this invention contains no γ-globulin that has been subjected to enzymolysis or chemical modification and is substantially of naturally occurring form, it has the advantages of long half-life in blood, no trouble due to antigenicity, and moreover of excellent solubility and high stability against deterioration with time. Thus, it is highly advantageous as a γ-globulin preparation for intravenous administration.

This invention will be illustrated in detail below with reference to an Example and Test Example, but it is not limited thereto.

In the Examples, the measles antibody titer was determined by the hemagglutination inhibition test and expressed in terms of the international unit (IU/100 mg). The anticomplement activity was determined according to Kabatt and Meyer {Experimental Immunochemistry, 225 (1961)} and Nishioka and Okada {Men'eki no Seikagaku (Biochemistry of Immunity), 103 (1971) (published by Kyoritsu Shuppan, Inc., Japan)}. Namely, 100 units of a complement was mixed with a sample to be tested, and the units remaining after decreasing was measured. The anticomplement activity was expressed in terms of the decrease in units.

EXAMPLE

A γ-globulin for intravenous administration (measles antibody titer: 9.2 IU/100 mg, anticomplement activity: 15) fractionated by use of Polyethylene Glycol #4000 was dissolved in a 0.02 M acetate buffer solution, ph 7.0, containing 0.5% of sodium chloride to a protein concentration of 5% W/V. This solution was contaminated with 0.2% W/V of Polyethylene Glycol #4000 used in fractionation. Six thousand ml of the γ-globulin solution was passed through a column of 1000 ml volume packed with HIGH POROUS POLYMER-HP20 and the fractions containing γ-globulin were pooled. No Polyethylene Glycol #4000 was detected in these γ-globulin fractions according to the colorrimetric method already mentioned. Glucose was added to the pooled γ-globulin solution to give a concentration of 2% W/V, and the mixed solution was lyophilized. When 1000 mg of the lyophilized product was dissolved in 15 ml of distilled water for injection use, it dissolved readily. After being stored at 30° C. for 10 months, the dried preparation showed neither a decrease in antibody titer nor an increase in anticomplement activity.

EXPERIMENTAL EXAMPLE

To 100 ml of 5% W/V solution of the pooled γ-globulin obtained in Example 1 was added glucose to give glucose concentrations of 0.1, 0.5, 1, 3, and 10% W/V, respectively, and the solution was lyophilized to obtain a dried preparation. The γ-globulin solution showed a measles antibody titer of 9 IU/100 mg and an anticomplement activity of 15. No polyethylene glycol was detected by the colorimetry.

The dry preparation was stored aseptically at 30° C. for 5 days and then further for 5 months aseptically. The antibody titer and anticomplement activity were measured after each period. The results were as shown in the following table. Statistically significant effects were observed in each of the tests.

| Glucose added (% W/V) | 30° C., 5 days Storage | | 5 months Storage | |
|---|---|---|---|---|
| | Measles antibody titer | Anti-complement activity | Measles antibody titer | Anti-complement activity |
| 0.1 | 7.5 | 20 | 7.4 | 32 |
| 0.5 | 8.8 | 22 | 8.1 | 24 |
| 1 | 9.1 | 17 | 9.0 | 17 |
| 3 | 9.0 | 17 | 9.0 | 16 |
| 10 | 8.9 | 16 | 9.0 | 17 |
| 0 | 6 | 22 | 8.1 | 35 |

What is claimed is:

1. An intravenously administrable γ-globulin dry preparation obtained by fractionating human plasma using polyethylene glycol, which preparation is substantially free of any remaining polyethylene glycol, the preparation comprising γ-globulin and from 0.2 to 2.0 parts by weight, based on one part by weight of γ-globulin, of glucose to stabilize the γ-globulin.

2. A γ-globulin preparation of claim 1, wherein the γ-globulin preparation has measles antibody.

3. In a process for preparing a storage-stable, intravenously administrable γ-globulin dry preparation, which γ-globulin has been obtained by fractionating human plasma with polyethylene glycol and has been substantially freed of remaining polyethylene glycol, the improvement comprising:

(1) adding glucose to an aqueous solution of γ-globulin, which is substantially completely free of remaining polyethylene glycol and is suitable for intravenous administration, the amount of glucose added being from 0.2 to 2.0 parts by weight, based on one part of γ-globulin sufficient to stabilize the γ-globulin; and thereafter (2) lyophilizing the aqueous solution to produce a dry powder.

4. A method of claim 3, wherein the aqueous solution contains γ-globulin in an amount of 5 to 20% W/V in terms of protein.

* * * * *